(12) United States Patent
Brown

(10) Patent No.: US 6,375,469 B1
(45) Date of Patent: *Apr. 23, 2002

(54) ONLINE SYSTEM AND METHOD FOR PROVIDING COMPOSITE ENTERTAINMENT AND HEALTH INFORMATION

(75) Inventor: Stephen J. Brown, Woodside, CA (US)

(73) Assignee: Health Hero Network, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/394,219

(22) Filed: Sep. 13, 1999

Related U.S. Application Data

(63) Continuation of application No. 08/814,293, filed on Mar. 10, 1997, now Pat. No. 5,951,300.
(51) Int. Cl.[7] .......................... G09B 19/00; G09B 23/28
(52) U.S. Cl. ........................................ 434/236; 434/262
(58) Field of Search ............................ 434/118, 236, 434/237, 238, 262

(56) References Cited

U.S. PATENT DOCUMENTS

| | | | | |
|---|---|---|---|---|
| 5,304,112 A | * | 4/1994 | Mrklas et al. ................ | 600/27 |
| 5,307,263 A | * | 4/1994 | Brown ......................... | 600/301 |
| 5,879,163 A | * | 3/1999 | Brown et al. ................ | 434/236 |
| 5,951,300 A | * | 9/1999 | Brown ......................... | 434/236 |

* cited by examiner

*Primary Examiner*—John Edmund Rovnak
(74) *Attorney, Agent, or Firm*—Black Lowe & Graham PLLC

(57) ABSTRACT

On-line health education includes displaying composites of personalized health content and patient-selected entertainment. Suitable sources of entertainment include generally available web pages and television programs. Composites are spatial (for page displays) or temporal (for image sequence displays). Health content is customized to health and personal situations of individual patients, and replaces advertisements. Composites are generated on a central server in communication with an entertainment server and a health server. Amenable diseases or behaviors include diabetes, asthma, hypertension, cardiovascular disease, eating disorders, HIV, mental health disorders, smoking, and alcohol and drug abuse.

18 Claims, 6 Drawing Sheets

FIG. 3-A
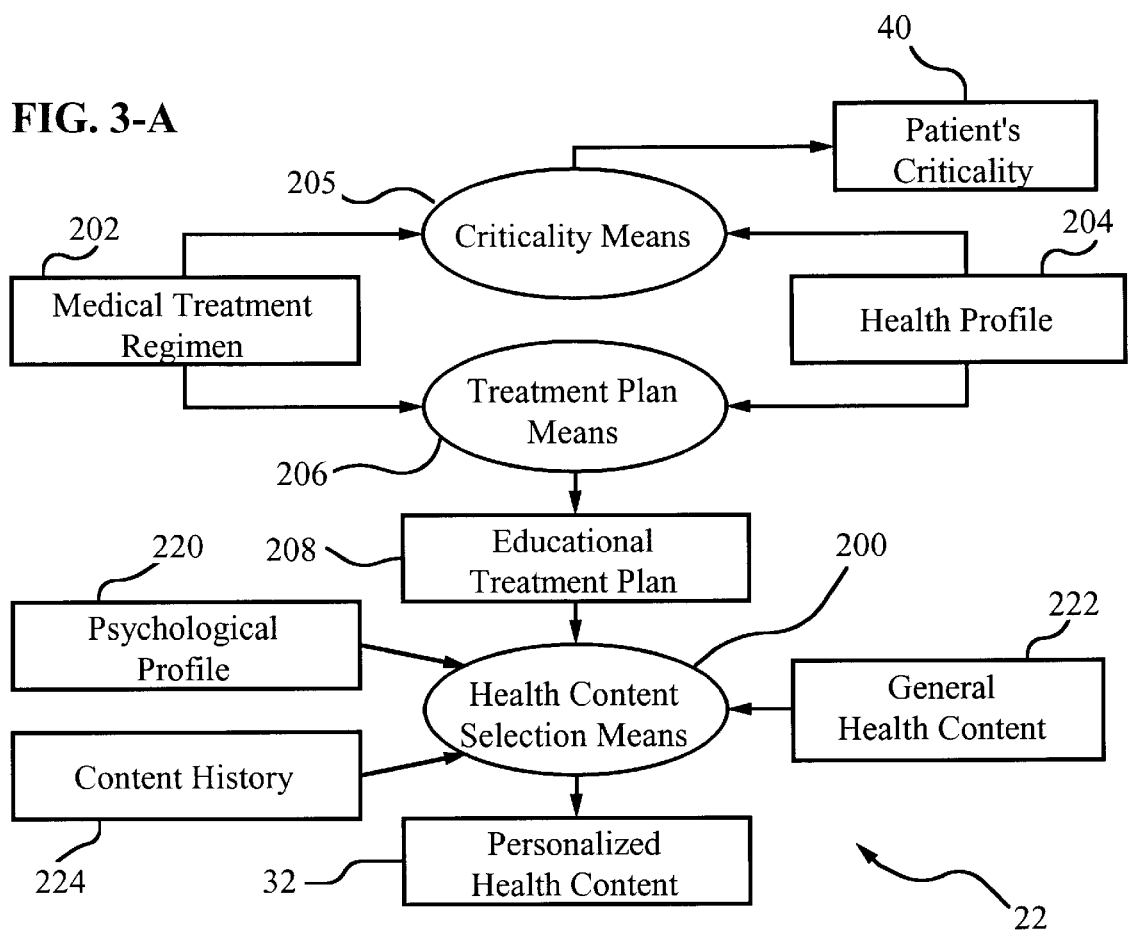

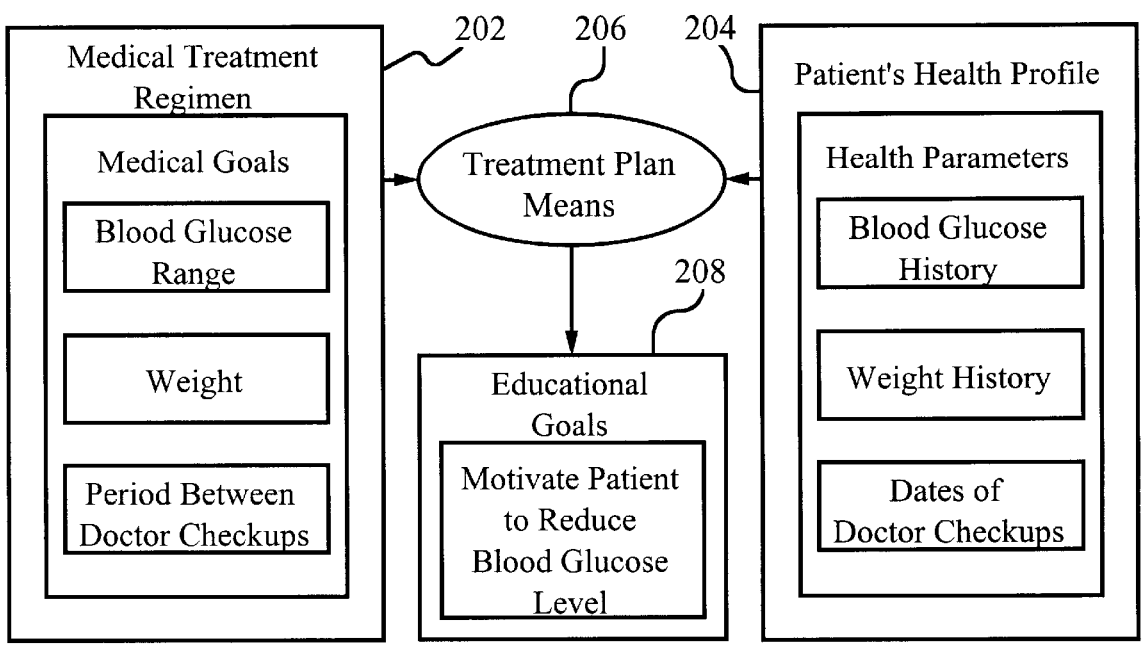
FIG. 3-B

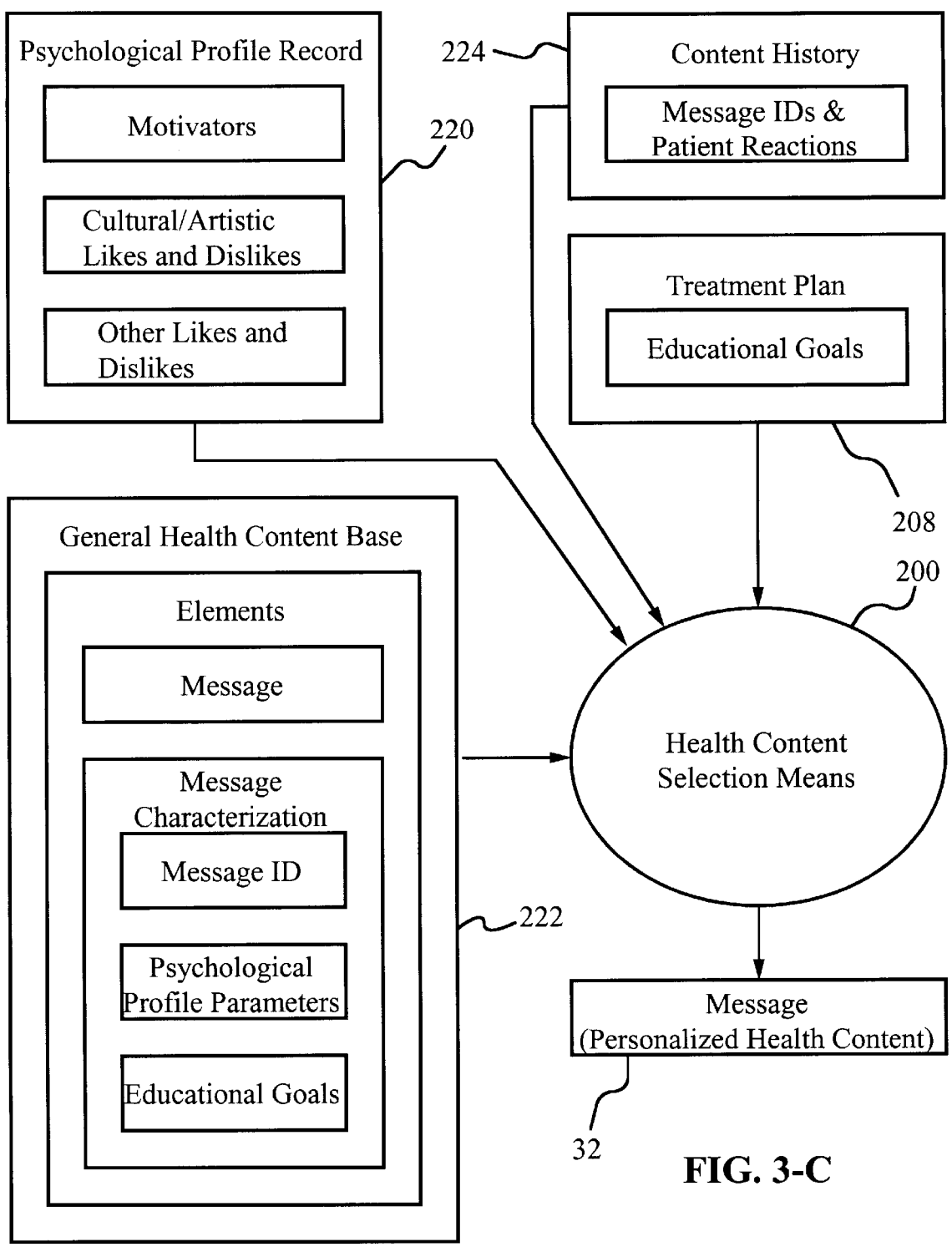
FIG. 3-C

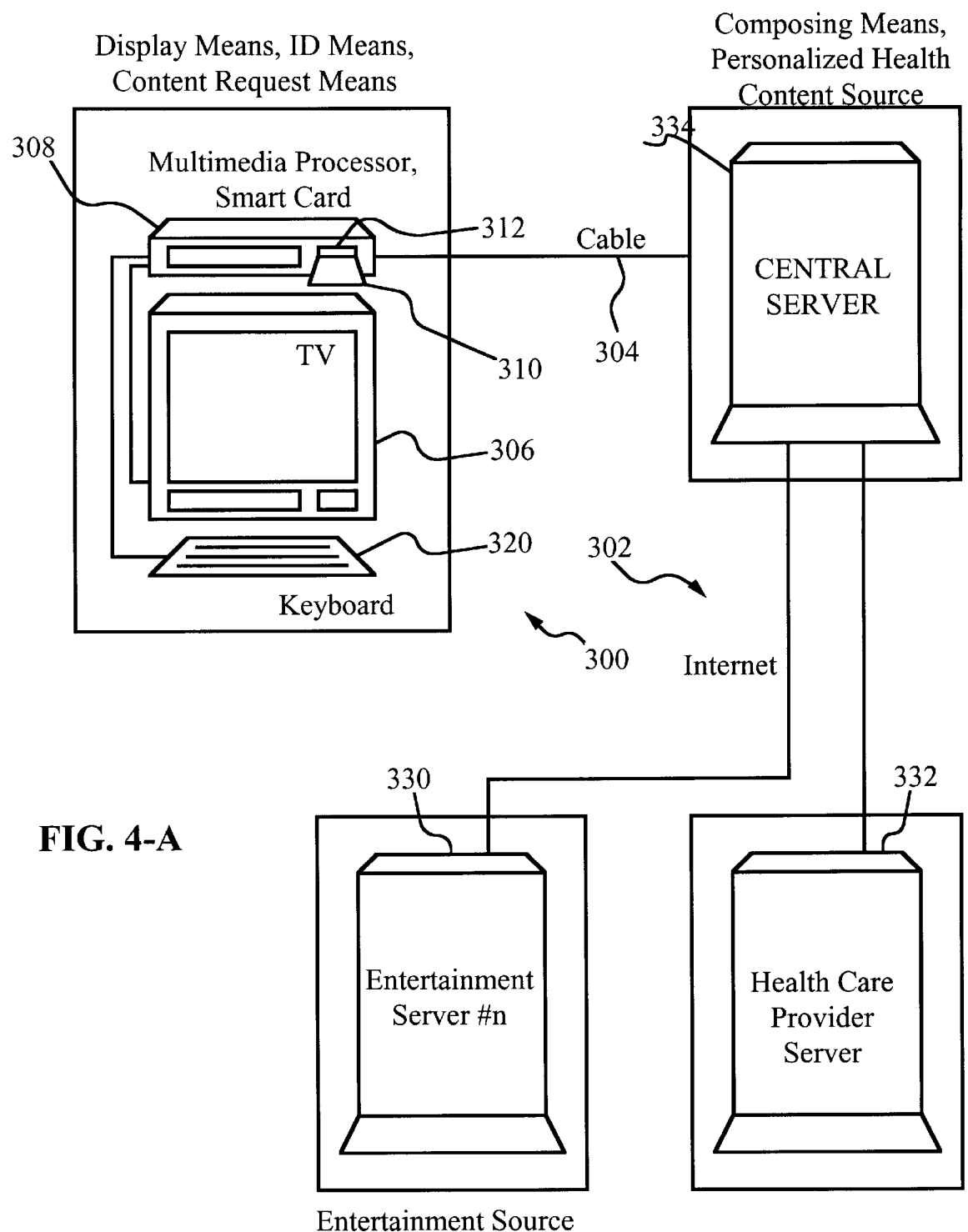
FIG. 4-A

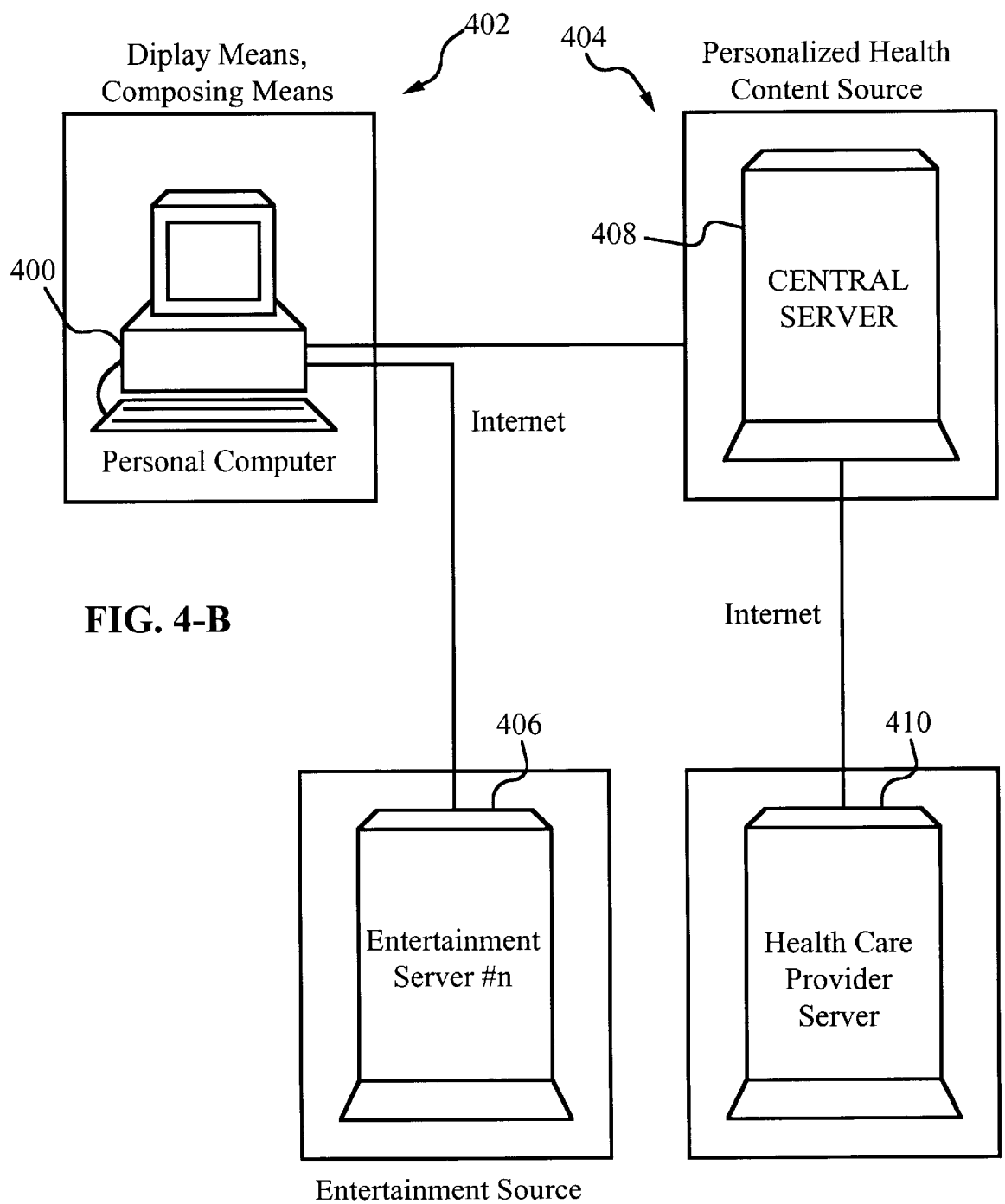
FIG. 4-B

ONLINE SYSTEM AND METHOD FOR PROVIDING COMPOSITE ENTERTAINMENT AND HEALTH INFORMATION

RELATED APPLICATION DATA

This invention is a continuation of Ser. No. 08/814,300 filed on Mar. 10, 1997 now U.S. Pat. No. 5,951,300 and relates to co-pending U.S. patent application Ser. No. 08/669,613 filed Jun. 24, 1996 now U.S. Pat. No. 5,879,163, are herein incorporated by reference.

FIELD OF THE INVENTION

This invention relates to the field of health education, and in particular to an on-line system and method for displaying to a patient a composite of patient-selected entertainment content and personalized educational health content.

BACKGROUND OF THE INVENTION

The health care community has recognized in recent years the importance of preventive care in managing patients' health. Preventive care is important for managing the health of patients having chronic diseases or long-term conditions, as well as for reducing the incidence of undesirable behavior (e.g. smoking) in at-risk patients. Preventive care includes educating patients about diseases and/or health consequences of behavior, ensuring communication between patients and health care providers (e.g. doctors), and providing patients with tools and/or treatments for managing diseases or behaviors.

Commonly used preventive care approaches suffer from several drawbacks. Much of preventive care is voluntary, and thus a large fraction of preventive care resources is typically spent on patients who actively seek involvement in their care. A large number of patients do not actively seek information and treatment in the absence of symptoms. Also, health care providers receive very little information on whether patients are complying with preventive care guidelines. Thus, health care providers often are not able to take remedial steps before the disease affects patients symptomatically (e.g. through pain). Reaching passive patients and people at risk for developing medical conditions is critical to delivering effective preventive care.

The mass-marketing techniques used for health education by most health maintenance organizations (HMOs) and insurance companies allow little customization of information to an individual patient's needs. Consequently, many patients may not directly identify with the educational approaches used by their health care providers. Personalizing health education would significantly raise the effectiveness of preventive health care, especially in children and adolescents.

In U.S. Pat. No. 5,542,420, Goldman et al. describe a system for prescribing personalized diets to individual patients. Health profiles of the patients are used to generate the personalized diets. The system described by Goldman et al. requires patient initiative in the prescription process.

In U.S. Pat. No. 5,140,419, Galumbeck et al. describe a multiple-hierarchical data delivery system capable of addressing receivers singly or in groups. The Galumbeck et al. patent does not discuss health education issues. Other related to selective addressing of receivers include U.S. Pat. Nos. 5,565,909 and 5,432,542 by Thibadeau et al., and U.S. Pat. No. 4,264,924 and U.S. Pat. No. 4,264,925 by Freeman et al.

None of the above-mentioned disclosures provides a system or method capable of delivering personalized health information to a patient, without requiring an express request for the information by the patient.

OBJECTS AND ADVANTAGES OF THE INVENTION

Accordingly, it is a primary object of the present invention to provide a system and method for delivering personalized health content to a patient, without requiring specific patient requests for the health content. The system allows delivering personalized health content in the course of normal recreational activities of the patient. Personalizing the health content improves the educational effectiveness of the method. The system allows the use, without substantial modification, of pre-existing spatial or temporal layouts of entertainment programming. The use of a dedicated server for data processing and storage allows a reduction in the amount of data transferred over relatively low-bandwidth communication lines to patients' homes.

SUMMARY OF THE INVENTION

A system for delivering personalized health information comprises a source of personalized health content, a source of entertainment content, a composing means in communication with the sources of entertainment and personalized health content, and a display means in communication with the composing means The composing means generates a composite of entertainment content and personalized health content. The display means generates a display of the composite.

The source of entertainment content is in communication with a content request means for allowing the patient to expressly request specific entertainment content, i.e. to "pull" content from the source of entertainment content. The entertainment content is delivered to the composing means following an express patient request for the entertainment content The source of personalized health content comprises a health content selection means in communication with a set of inputs. The health content selection means generates the personalized health content according to data from the set of inputs. The set of inputs comprises a general health content base and inputs allowing the selection of content from the general health content base. Inputs used for content selection include a medical treatment regimen, a health profile, an educational treatment plan, a psychological profile, and a content history of the patient. A treatment plan means generates the educational treatment plan from the treatment regimen and health profile of the patient.

The medical treatment regimen specifies target health parameters, while the health profile specifies actual health parameters of the patient. The treatment plan is generated by comparing the target parameters to the actual parameters. The treatment plan specifies educational goal parameters of the patient. The educational goal parenters measure the importance of corresponding educational goals for the particular patient. The psychological profile comprises data characterizing likes, dislikes, and motivators of the patient. The content history identifies the health content to which the patient has been exposed within a given time period.

The composing means generates the composite according to a patient criticality. The patient criticality measures the patient's compliance with the treatment regimen. A criticality means generates the patient criticality by comparing the treatment regimen and the health profile.

The composite is preferably a spatial composite. That is, the composite comprises a composite page including both entertainment and health content. The composite page comprises an entertainment section comprising the entertainment content and a health section comprising the health content. The source of entertainment content generates an original page comprising an entertainment section and an undesirable section (e.g. an advertisement). The composing means replaces the undesirable section with a health section, thereby generating the composite page. The page layout of the composite page is substantially identical to the page layout of the original page. A spatial composite preferably comprises a hypertext markup language (HTML) document.

In an alternative embodiment suited for television health education, the composite is a temporal composite. The display of the composite then comprises an image sequence comprising a first image and a second image, wherein the first image comprises the entertainment content and the second image comprises the health content. The first image consists substantially of the entertainment content, while the second image consists substantially of the health content.

The system comprises a client subsystem comprising the display means, and a server subsystem in communication with the client, subsystem over a remote network. The display means preferably comprises a television set and a multimedia processor. Suitable remote networks include the Internet and communications lines used for cable television delivery. The server subsystem preferably comprises the composing means and the entertainment and health content sources. The server subsystem, and in particular the source of health content, is in communication with a plurality of client subsystems, where each client subsystem corresponds to a different patient, and where data is customized (personalized) independently for each client subsystem.

The present invention further provides a method of delivering health information to a patient. The method comprises the steps of generating the composite of personalized health content and patient-requested entertainment content, and displaying the composite to the patient.

DESCRIPTION OF THE FIGURES

FIG. 3-A is a block diagram illustrating a preferred method of generating a patient criticality and personalized health content, according to the present invention.

FIG. 3-B is a block diagram exemplifying structures for a medical treatment regimen, health profile, and educational treatment plan for a diabetes patient, according to the present invention.

FIG. 3-C is a block-diagram exemplifying preferred structures for a general health content base, psychological profile, and content history, according to the present invention.

FIG. 4-A shows preferred hardware and connections for a system of the present invention.

FIG. 4-B shows an alternative arrangement of hardware according to a system of the present invention.

DETAILED DESCRIPTION

In the following description, a source of content is understood to include a record of the content (e.g. a HTML file), or hardware used to store the content (e.g. a server). Personalized health content is understood to refer to health content that is personalized to an individual patient's health situation, and not merely to a health situation of a generic patient having a given disease. In a system for delivering health information to a plurality of patients, personalized health content is understood to refer to health content customized individually for each patient. The statement that an input is in communication with some data processing means is understood to mean that the data processing means is adapted to use (directly or indirectly) data specified by the input. The term server is understood to refer to an information-generating device capable of communicating with a plurality of clients; servers include computer servers and television delivery systems. The term patient is understood to refer to persons suffering from a condition or disease, as well as persons at risk for engaging in behavior having adverse health consequences.

The following discussion will focus on a computer-based implementation of a system and method for diabetes preventive health care. It will be clear to the skilled artisan that the present invention is suitable for preventive care directed to many other health conditions. Moreover, there are many well known structures, interfaces and processes that are suitable for implementing the present invention.

Figure 1:
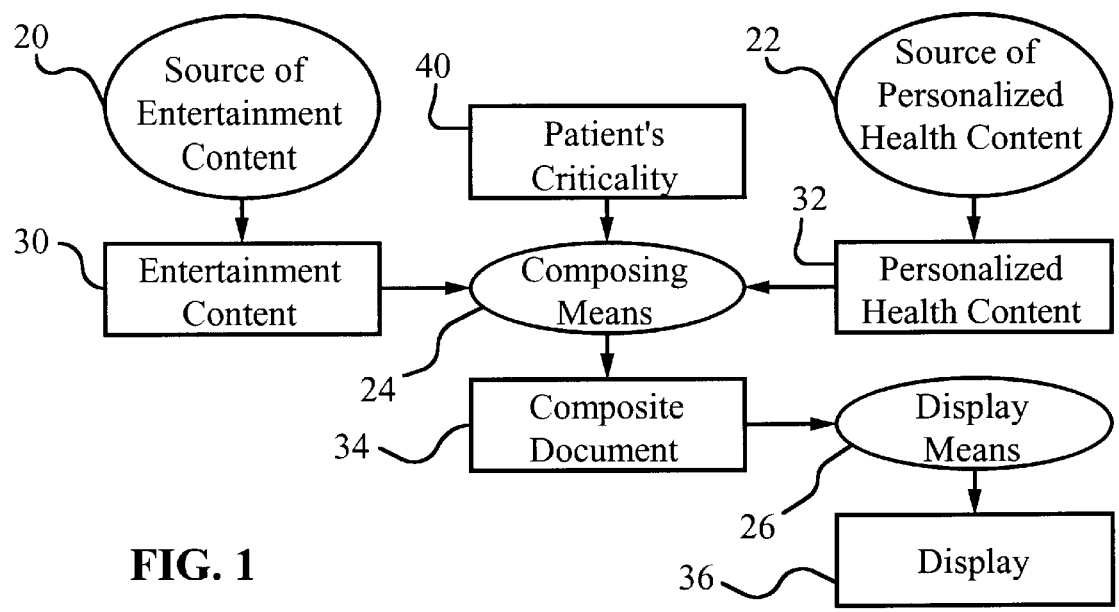
FIG. 1 is a high-level block diagram illustrating the operation of a system of the present invention.

FIG. 1 illustrates generally a health information delivery system of the present invention. A source of entertainment content 20 and a source of personalized health content 22 are in communication with a composing means 24, which in turn is in communication with a display means 26. Source 20 generates entertainment content 30, while source 22 generates personalized health content 32. Composing means 24 generates a composite document 34 comprising entertainment content 30 and personalized health content 32. Display means 26 generates a display 36 of composite document 34. A patient criticality or criticality data 40 is used by composing means 24 to modulate the relative display importance of health content 32 within display 36.

Preferably, entertainment content 30 comprises a hypertext markup language (HTML) document requested by the patient under treatment. Personalized health content 32 comprises an HTML document encoding a personalized educational health message, while composing means 24 comprises computer software. Composite document 34 is preferably a HTML file. Display means 26 comprises computer software (e.g. a browser) capable of generating displays of HTML documents. It will be apparent to the skilled artisan that, in general, many formats other than HTML are available for entertainment content 30, personalized health content 32, and composite document 34.

Figure 2:
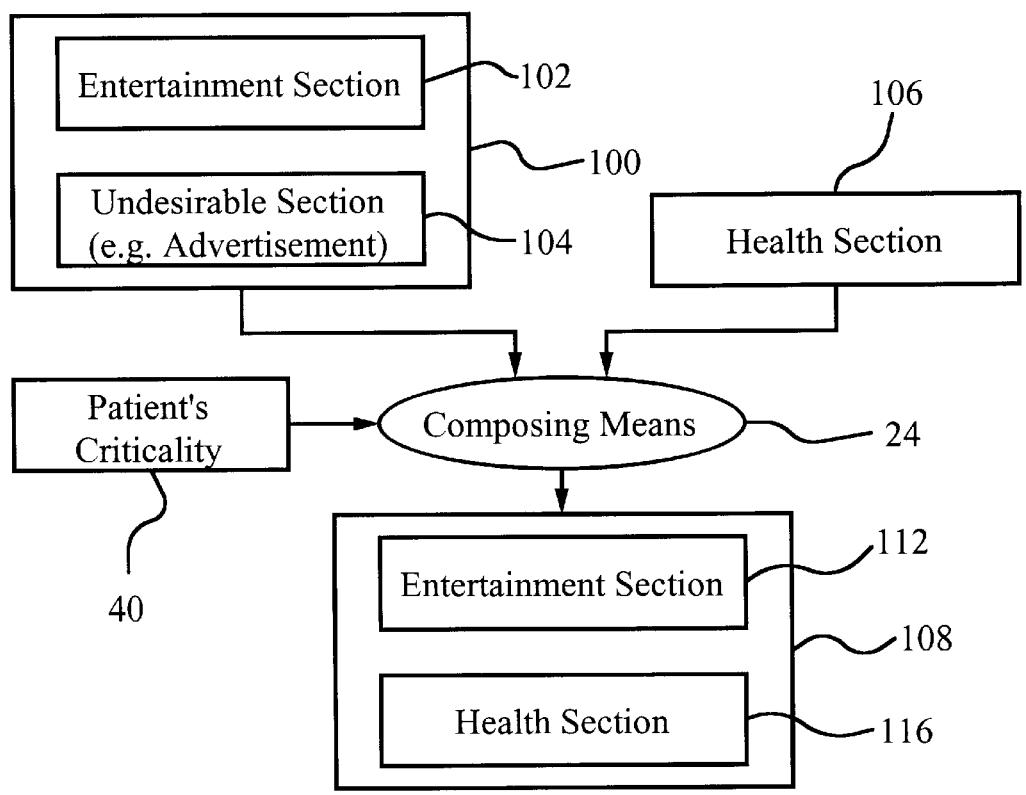
FIG. 2 illustrates the generation of a composite page by substitution of a health section for an undesirable section in an original page, according to the present invention.

The composite is preferably a spatial composite. That is, entertainment and health content are displayed within the same composite page or image. FIG. 2 illustrates the generation of a spatial composite according to a preferred embodiment of the present invention. A conventional HTML entertainment document comprises an original page 100. Original page 100 comprises an entertainment section 102 and an undesirable section 104. Page 100 is a conventional web page such as a home page of a company or information provider. Undesirable section 104 comprises an advertisement not requested by the patient, or other information targeted for replacement.

Composing means 24 uses page 100 and a health section.106 to generate a page 108. Composite page 108 comprises an entertainment section 112 and a composite health section 116. Preferably, entertainment section 112 is identical to entertainment section 102. Composing means 24 thus essentially replaces undesirable section 104 with health section 116. Health section 116 is preferably formatted to have substantially the same size as undesirable section 104, such that the page layout of composite page 108 is similar to the page layout of original page 100. Health section 116 comprises a link to further information related to the subject of health section 116; the patient accesses the link by clicking on health section 116. In an alternative embodiment (not illustrated), a composite page is generated by adding a health section to an original page, without removing any undesirable section from the original page.

Generating page sections of predetermined size using HTML is well known in the art. Generating HTML composites and recognizing advertising sections of HTML documents are described in detail in the above-incorporated U.S. Patent Application "System and Method for Modifying Documents Sent Over a Communications Network."

Criticality data 40 modulates the mixing of entertainment section 102 and health section 106. Criticality data 40 measures the patient's compliance with a doctor-prescribed treatment regimen. Criticality data 40 modulates the relative display importance of section 116 within page 108. The relative display importance preferably includes the probability that undesirable section 104 is replaced by health section 116. For a patient managing his or her health successfully, composite page 108 may include a limited number of health sections 116 and a relatively large number of advertising sections. For a patient not in compliance with the treatment regimen, composite page 108 includes a large number of health sections 116. In another embodiment, relative display importance includes the size and placement of health section 116 within page 108; the page layout of composite page 108 is then generally different from the page layout of original page 100.

FIG. 3-A illustrates the steps used to generate personalized health content 32 in a preferred embodiment of the present invention. Source 22 of personalized health content 32 comprises a health content selection means 200 in communication with a set of inputs. The set of inputs provides data for generating personalized health content 32.

The set of inputs of selection means 200 comprises a base 222 of general health content 222. General health content 222 is generated and updated using research on communicating health information. The general health content base is preferably a large database of messages comprising video, audio, hypertext, and/or text-to-speech data. Each element of the general health content base comprises a message and a message characterization, as illustrated in FIG. 3-C. The message characterization comprises an explicit or implicit description of the message. In particular, the message characterization comprises information on the treatment plans and psychological and/or health profiles for which the message is suitable or effective. In a preferred embodiment, the message characterization comprises tags indicating the effectiveness of the corresponding message for given treatment plan, psychological profile, and health profile parameters.

The set of inputs of selection means 200 comprises a patient psychological profile 220, as shown in FIG. 3-A. Psychological profile 220 contains information about the patient's psychology, including his or her likes, dislikes, and motivators. For example, psychological profile 220 includes parameters characterizing the patient's response to various motivating factors such as love of family or fear of adverse health consequences, and the patient's interest for cultural or artistic subjects such as football or jazz music. The data of psychological profile 220 is gathered from tests of the patient, from questionnaires, and by monitoring the patient's usage of the system. Psychological profile 220 records the subjects corresponding to the health sections on which the patient has requested information (by clicking on the sections).

Selection means 200 compares parameters of psychological profile 220 with corresponding parameters of message characterizations. Selection means 200 then tends to select for display messages which fit the patient's psychological profile. For example, for a diabetes patient motivated by fear of adverse future health consequences, selection means 200 is likely to select messages describing long term adverse health consequences (e.g. blindness, amputation) resulting from poor diabetes health care. For a patient motivated by money, selection means 200 tends to select messages that communicate the financial benefits of maintaining blood glucose levels within prescribed ranges. For a patient motivated by love of family, selection means 200 tends to select messages emphasizing the importance of proper care to the patient's family. In general a patient responds to a plurality of motivational factors.

The set of inputs further comprises a medical treatment regimen 202. Treatment regimen 202 preferably comprises a set of doctor-prescribed target health parameters for the patient.

For a diabetes patient, such parameters include target range of blood glucose levels, weight, exercise times, parameters characterizing the patient's diet, and recommended period between doctor checkups.

The set of inputs further comprises a health profile 204 of the patient. Health profile 204 comprises a set of actual health parameters of the patient. At least some of the actual health parameters defined by health profile 204 correspond to the target health parameters of treatment regimen 202. For a diabetes patient, health profile 204 includes a history of the patient's blood glucose reading, as well as the patient's weight, age, date of last doctor checkup, and other information relevant to the patient's health. Suitable parameters for characterizing diseases other than diabetes can be readily determined by an artisan of average skill.

A criticality means 205 generates criticality 40 by comparing treatment regimen 202 and health profile 204. Preferably, criticality 40 comprises a criticality index that measures differences between actual health parameters of the patient (as reflected in health profile 204) and corresponding recommended health parameters of the patient (as determined from treatment regimen 202). For example, for a diabetes patient the criticality index increases if the patient's current blood glucose reading is not within a prescribed range, or if the period since the patient's last doctor checkup is longer than the recommended period between doctor checkups. Exact dependencies of criticality indices on actual and recommended health parameters can be readily determined by the skilled artisan according to the disease under treatment and the medical data available for the patient.

A treatment plan means 206 generates an educational treatment plan 208 from treatment regimen 202 and health profile 204. FIG. 3-B illustrates schematically an example of the generation of an educational treatment plan for a diabetic patient. Educational treatment plan 208 is an educational prescription customized to the patient's current health situation. Educational treatment plan 208 includes a set of parameters characterizing the importance of various health goals for the treatment of the patient. For example, if the patient's blood glucose readings are higher than the range prescribed by the patient's doctor (specified by regimen 202), an important educational goal of treatment plan 208 is to motivate the patient to reduce his or her blood glucose levels.

Educational treatment plan 208 is an input for health content selection means 200. Health content selection means 200 compares parameters of educational treatment plan 208 with corresponding parameters of message characterizations. Selection means 200 then tends to select messages which fit the patient's educational treatment plan 208. For example, if a goal of treatment plan 208 is to motivate the patient to reduce his or her blood glucose level, selection means 200 tends to select messages relating to blood glucose level.

The set of inputs of selection means 200 further comprises a content history 224 of the patient. Content history 224 keeps track of which messages the patient has seen, and whether the patient requested additional information in response to each message. Content history 224 allows the delivery of complementary and non-repetitive messages to the patient, over time. Some content is designed to be delivered over a series of messages. Content history 224 allows the delivery of predetermined sequences of messages, and in particular of content designed to be delivered over time. Content history 224 is used to update psychological profile 220 according to the subjects of the messages in response to which the patient has requested additional information.

FIG. 3-C illustrates an example of the selection by selection means 200 of a message from general health content base 222. Selection means 200 preferably compares the message characterizations of each message to the data characterizing a patient profile, and selects for composing messages whose characterizations match the patient profile. The patient profile includes the patient's educational treatment plan 208, content history 224, and health and psychological profiles 204 and 220, respectively.

FIG. 4-A illustrates the hardware and connections in a system for delivering personalized health information, according to a preferred embodiment of the present invention. The system comprises a client subsystem 300 located at the patient's home, and a server subsystem 302 capable of communication over a remote network with client subsystem 300. The remote network preferably comprises a communications line 304 conventionally used for delivery of cable television programming. Preferably, server subsystem 302 is in communication with a plurality of different client subsystems 300. The information delivered by server subsystem 302 is individually personalized for each client subsystem 300.

Client subsystem 300 comprises display means 26 for a particular patient. Display means 26 preferably includes a television set 306 connected to a multimedia processor 308. A patient identification means 310 is capable of communication with multimedia processor 308. Patient identification means 310 comprises a data-bearing card, or "smart card". Multimedia processor 308 has a receiving slot 312 for receiving card 310. Card 310 contains an encrypted patient code identifying the patient, as well as an address of server subsystem 302 for allowing client subsystem 300 to connect to server subsystem 302. The address preferably comprises a URL address.

A patient feedback means is in communication with multimedia processor 308. The patient feedback means preferably comprises a keyboard 320. The patient feedback means allows the patient to request a specific entertainment page, by transmitting to server subsystem 302 the URL address of the entertainment page. The patient feedback means also allows the patient to update psychological profile 220 and health profile 204.

Server subsystem 302 preferably comprises an entertainment server 330 for generating entertainment content, a health server 332 comprising inputs for generating health data on the patient, and a central server 334 for generating personalized health content and the composite of entertainment and personalized health content. Health server 332 is preferably a database located at the patient's health care provider. Health server 332 contains the patient's health profile, standards of care for the patient's disease, and the medical treatment regimen prescribed by the patient's doctor. Central server 334 is connected to entertainment server 330 and health server 332 over the Internet. Central server 334 is connected to multimedia processor 308 over communications line 304.

The patient feedback means sends to central server 334 a request for an entertainment document (e.g. an HTML file) located on entertainment server 330. The entertainment document is any document generally available to the patient. For a page-based implementation, suitable entertainment documents include home pages of companies or organizations, Internet directories, and pages containing sports news or stock quotes. Central server 334 retrieves the entertainment document from entertainment server 330 and generates a composite document by splicing a health message into the entertainment document as described above. Central server 334 then sends the composite document to display means 26 for display.

FIG. 4-B illustrates the hardware and connections in an alternative embodiment of the present invention. The display means comprises a computer 400 and conventional browsing software (e.g. the Navigator® from Netscape Communications) installed on computer 400. The composing means comprises an extension to the browsing application. A client subsystem 402 comprises computer 400, while a server subsystem 404 comprises an entertainment server 406, a central server 408 and a health server 410. Client subsystem 402 comprises the display and composing means, while server subsystem 404 comprises the sources of entertainment and personalized health content.

In yet another embodiment of the present invention, the display means comprises a conventional television set connected to a cable television delivery system capable of delivering individualized programming to each of the system's subscribers. The source of entertainment content comprises a television program, while the source of personalized health content comprises a personalized educational health message. The composing means comprises conventional equipment suitable for splicing the health message within the television program. In such a television-based implementation, the composite is preferably a temporal composite. That is, the composite display comprises an image sequence, with the entertainment and health content displayed within distinct images.

It will be clear to one skilled in the art that the above embodiment may be altered in many ways without departing from the scope of the invention. Various relative arrangements of inputs and processing means are suitable for generating personalized health content. The patient criticality can be used as an input for the health content selection means. Various diseases or behaviors are amenable to preventive care according to a method of the present invention, including asthma, hypertension, cardiovascular disease, eating disorders, HIV, mental health disorders, smoking, and drug or alcohol abuse. Personalizing the health content can be achieved in the process of generating (rather than selecting) the health content. The health content need not contain only predetermined educational messages; suitable health content includes data from the patient's health profile. Accordingly, the scope of the invention should be determined by the following claims and their legal equivalents.

What is claimed is:

1. A system for delivering health information to a patient, comprising:
   a) a first source for providing personalized health content;
   b) a second source for providing an original page, said original page comprises an entertainment section and an undesirable section;
   c) a compliance determiner for determining a patient's compliance with a predefined treatment regimen, said patient's compliance is determined by comparing said treatment regimen and a health profile preassigned to the patient;
   d) a composer for determining display importance according to said determined patient's compliance and for generating a composite page by combining said original page with said personalized health content according to said determined display importance, wherein said personalized health content is transmitted from said first source to said composer via a remote network; and
   e) a display in communication with said composer, for generating a display of said composite page.

2. The system of claim 1, wherein said composite page comprises at least one health section comprising said personalized health content.

3. The system of claim 2, wherein said composer determines the size and position of the at least one health section in the generated composite page according to the determined display importance.

4. The system of claim 2, wherein said composer determines the ratio of undesirable sections to health sections in the composite page according to the determined display importance.

5. The system of claim 1, wherein said first source comprises a set of inputs and a health content selector for generating said personalized health content according to data from said set of inputs, wherein said set of inputs comprises a general health content base comprising elements and wherein each element of said general health content base comprises a message and a message characterization.

6. The system of claim 5, wherein said message characterization comprises at least one effectiveness tag for indicating the effectiveness of the corresponding message for at least one of a particular predefined treatment plan, psychological profile or health profile parameter.

7. The system of claim 1, wherein said first source comprises a set of inputs and a content selector for generating said personalized health content according to data from said set of inputs, wherein said set of inputs comprises a patient psychological profile and a general health content base, wherein said general health content base comprises elements and each element of said general health content base comprises a message and a message characterization.

8. The system of claim 7, wherein said patient psychological profile comprises parameters associated with patient's response to various motivating factors and interest in various subjects, wherein said psychological profile parameters being determined according to previously gathered patient information and patient usage of the system.

9. The system of claim 8, wherein said content selector generates said personalized health content by selecting a message according to a comparison between said parameters of said psychological profile with said message characterizations.

10. A method for delivering health information to a patient, comprising:
   transmitting personalized health content and an original page over a remote network, said original page comprises an entertainment section and an undesirable section;
   determining a patient's compliance with a predefined treatment regimen, said patient's compliance is determined by comparing said treatment regimen and a health profile preassigned to the patient;
   determining display importance according to said determined patient's compliance;
   generating a composite page by combining said original page with said personalized health content according to said determined display importance, wherein said personalized health content is received via said remote network; and
   generating a display of said composite page.

11. The method of claim 10, wherein said composite page comprises at least one health section comprising said personalized health content.

12. The method of claim 11, wherein generating a composite page further determines the size and position of the at least one health section in the composite page according to the determined display importance.

13. The method of claim 11, wherein generating a composite page further determines the ratio of undesirable sections to health sections in the composite page according to the determined display importance.

14. The method of claim 10, further comprising generating said personalized health content according to data from a set of inputs, wherein said set of inputs comprises a general health content base comprising elements and wherein each element of said general health content base comprises a message and a message characterization.

15. The method of claim 14, wherein said message characterization comprises at least one effectiveness tag for indicating the effectiveness of the corresponding message for at least one of a particular predefined treatment plan, psychological profile or health profile parameter.

16. The method of claim 10, further comprising generating said personalized health content according to data from a set of inputs, wherein said set of inputs comprises a patient psychological profile and a general health content base, wherein said general health content base comprises elements and each element of said general health content base comprises a message and a message characterization.

17. The method of claim 16, wherein said patient psychological profile comprises parameters associated with patient's response to various motivating factors and interest in various subjects, wherein said psychological profile parameters being determined according to previously gathered patient information and patient usage.

18. The method of claim 17, wherein generating said personalized health content comprises generating said personalized health content by selecting a message according to a comparison between said parameters of said psychological profile with said message characterizations.

* * * * *